United States Patent [19]

Chastagner

[11] Patent Number: 5,152,748
[45] Date of Patent: Oct. 6, 1992

[54] MEDICAL CATHETERS THERMALLY MANIPULATED BY FIBER OPTIC BUNDLES

[76] Inventor: Philippe Chastagner, 608 Aumond Rd., Augusta, Ga. 30909

[21] Appl. No.: 663,496

[22] Filed: Mar. 4, 1991

[51] Int. Cl.⁵ .............................................. A61M 37/00
[52] U.S. Cl. ........................................ 604/95; 604/281
[58] Field of Search .......................... 604/95, 280-282, 604/270; 128/4; 606/78

[56] References Cited

U.S. PATENT DOCUMENTS

| | | | |
|---|---|---|---|
| 4,543,090 | 9/1985 | McCoy | 604/95 |
| 4,753,223 | 6/1988 | Bremer | 128/4 |
| 4,799,474 | 1/1989 | Ueda | 128/4 |
| 4,838,859 | 6/1989 | Strassman | 604/95 |
| 4,934,340 | 6/1990 | Ebling et al. | 128/6 |
| 4,944,727 | 7/1990 | McCoy | 604/95 |
| 5,019,040 | 5/1991 | Itaoka et al. | 604/95 |

*Primary Examiner*—C. Fred Rosenbaum
*Assistant Examiner*—C. Maglione
*Attorney, Agent, or Firm*—Dixon, Harold M.; William R. Moser; Richard E. Constant

[57] ABSTRACT

A maneuverable medical catheter comprising a flexible tube having a functional tip. The catheter is connected to a control source. The functional tip of the catheter carries a plurality of temperature activated elements arranged in parallel and disposed about the functional tip and held in spaced relation at each end. These elements expand when they are heated. A plurality of fiber optic bundles, each bundle having a proximal end attached to the control source and a distal end attached to one of the elements carry light into the elements where the light is absorbed as heat. By varying the optic fiber that is carrying the light and the intensity of the light, the bending of the elements can be controlled and thus the catheter steered. In an alternate embodiment, the catheter carries a medical instrument for gathering a sample of tissue. The instrument may also be deployed and operated by thermal expansion and contraction of its moving parts.

12 Claims, 3 Drawing Sheets

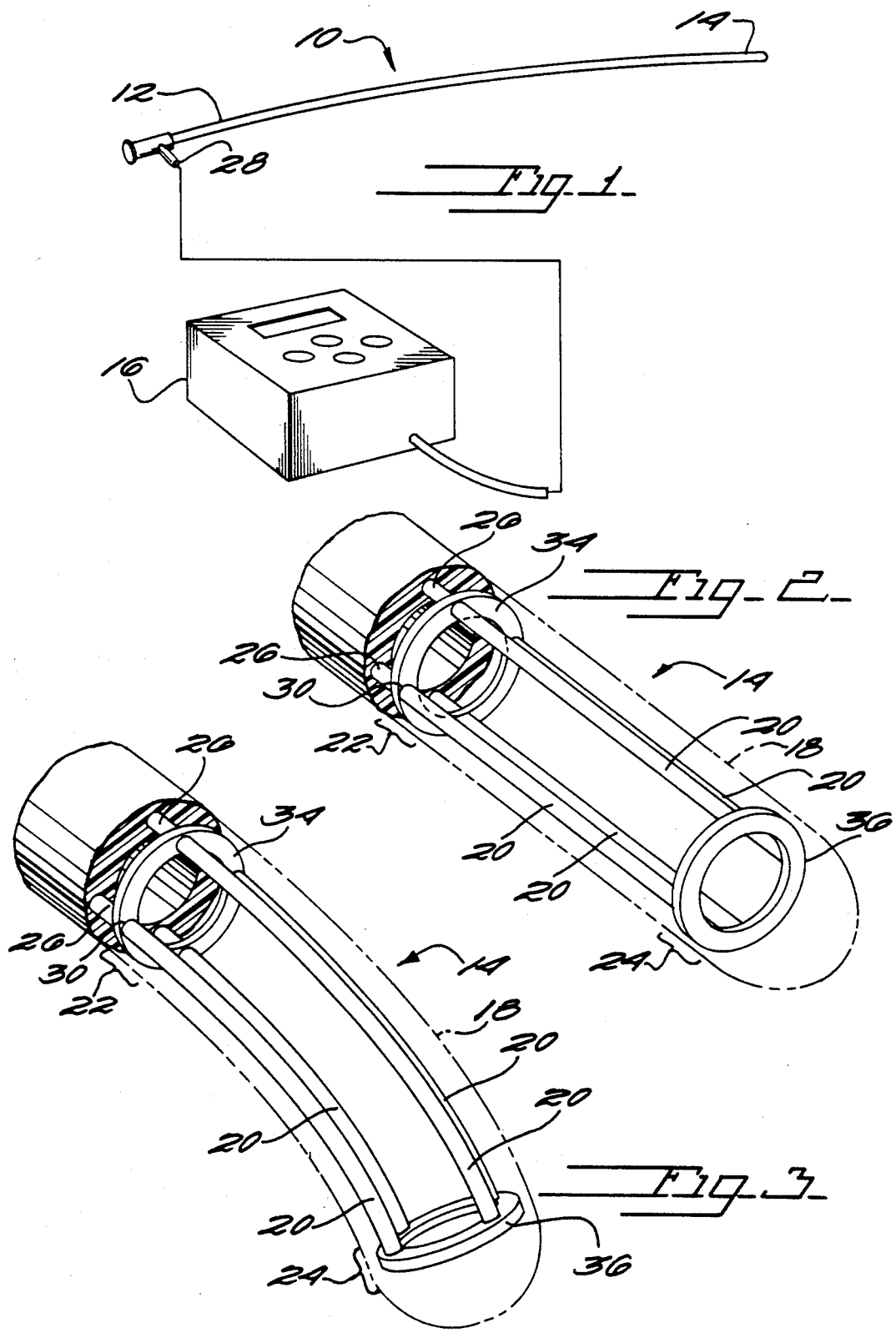

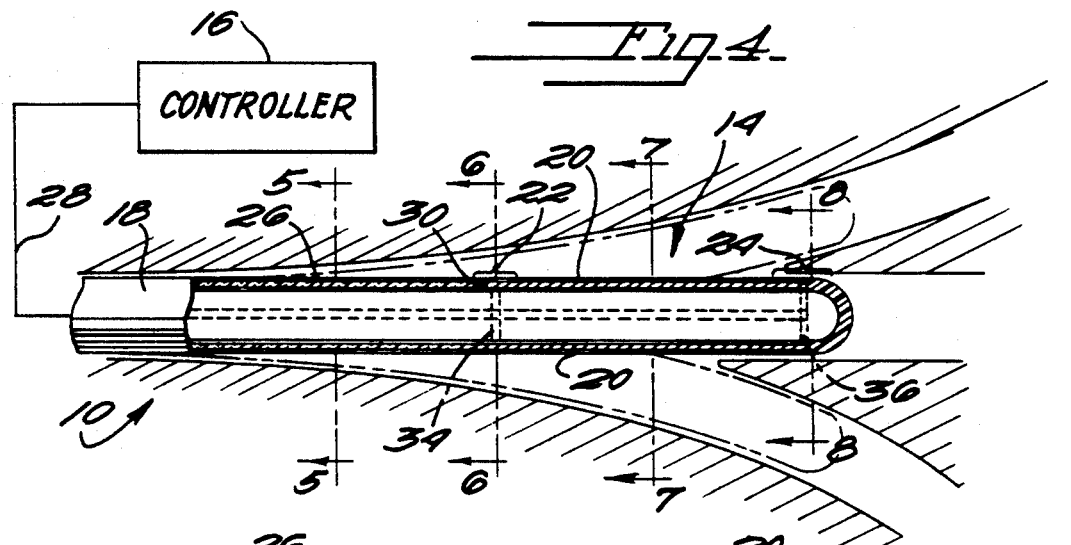
Fig. 4
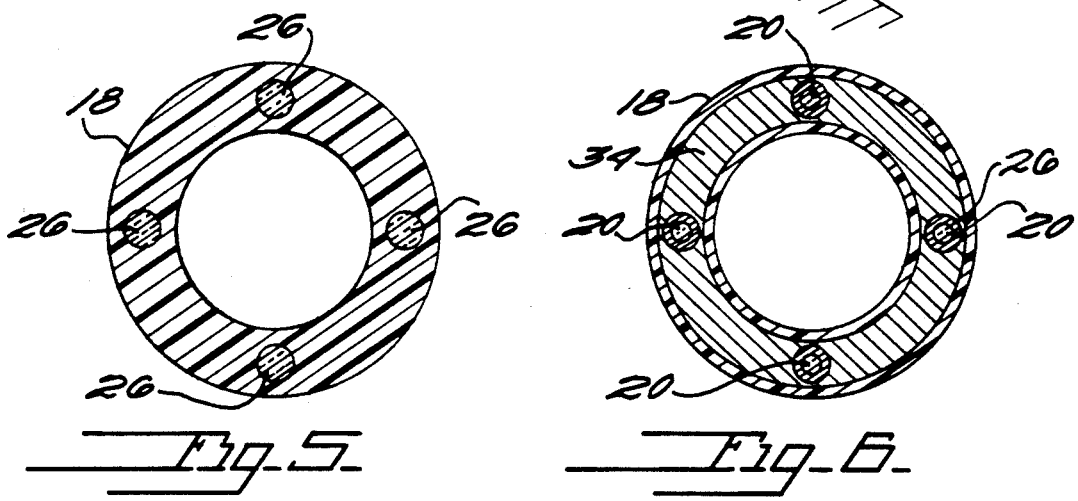
Fig. 5
Fig. 6
Fig. 7
Fig. 8

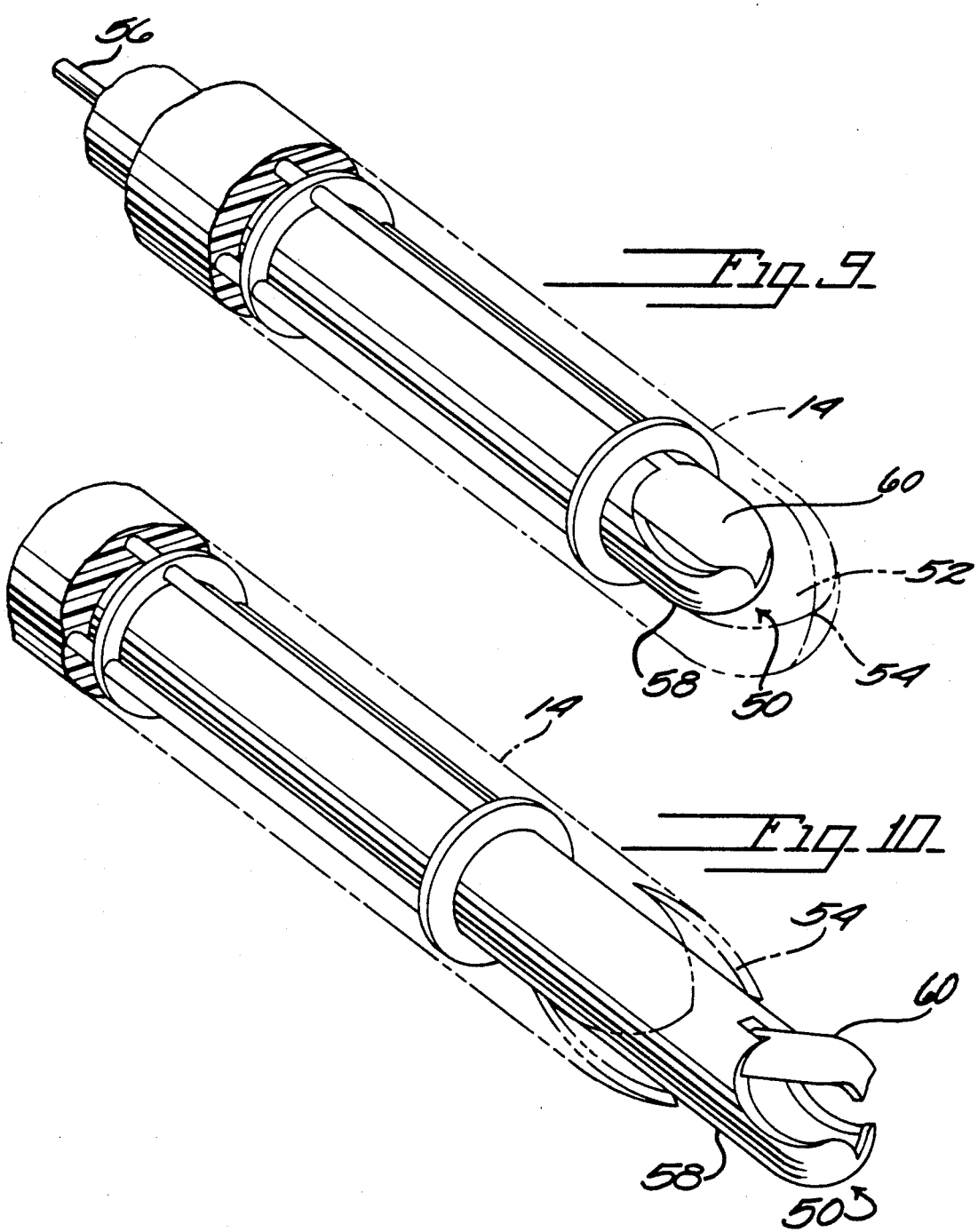

MEDICAL CATHETERS THERMALLY MANIPULATED BY FIBER OPTIC BUNDLES

The United States Government has rights in this invention pursuant to Contract No. DE-AC09-89SR18035 between the U.S. Department of Energy and Westinghouse Savannah River Company.

BACKGROUND OF THE INVENTION

1. Field of the Invention:

The present invention relates to medical catheters and more particularly to catheters that are maneuverable through anatomical cavities, vessels, and other structures of the body.

2. Discussion of Background:

Generally, the term "catheter" encompasses a wide array of devices for accessing remote locations, particularly within interior bodily vessels and cavities. Medical catheters may be used for tissue sampling, temperature measurements, drug administration, or electrical stimulation to a selected tissue. With fiber optics, they may carry light for visual inspection of tissues. Catheters may also be used in industrial environments to inspect the otherwise inaccessible interiors of equipment.

One serious drawback in using catheters is maneuvering them in the desired direction. Catheters are pushed, rather than pulled, and therefore tend to move in a straight line unless they are warped or meet with resistance, in which case they move in a less resistive direction. If the path is relatively straight and nondiverging, maneuvering is less of a problem. However, in blood vessels, for example, maneuvering into the correct branch of an artery can be quite difficult. A catheter might be inserted into a femoral artery and advanced along the arterial system through numerous branches in order to arrive in a coronary artery. The catheter must be advanced carefully through paths that are not straight but do have bends and turns so as not to damage tissue. It is highly desirable to be able to steer the catheter to avoid tissue damage and to be able to select one path when more than one present themselves. Several techniques have been developed to maneuver a catheter.

Catheters with heat-activated "mechanical memory" elements are known. The temperature-activated element has a first memory shape and a second straightened shape. The catheter is placed in the pathway in the straightened shape and when electrically heated to a predetermined temperature, the element will undergo bending to the memory shape, thereby effecting the desired change in direction of the tip of the catheter. An example of such a device is found in U.S. Pat. No. 4,543,090.

Catheters with contracting members that undergo axial shortening when an electrical current is applied are also known. An example of this type catheter is set forth in U.S. Pat. No. 4,934,340. Other means of bending catheters utilize fluids or permanent magnets and magnetic fields.

Although such devices incorporate means for bending the tip of a catheter, they are less than optimal for certain medical procedures because they are difficult to control and manipulate and they are relatively bulky. Accordingly, there remains a need for a small, steerable, maneuverable catheter.

SUMMARY OF THE INVENTION

The present invention addresses the problems of maneuvering catheters within the body or within industrial equipment. The present invention is a catheter comprising a flexible tube having a functional tip at one end and connected to a control source at the other end. The functional tip contains a plurality of temperature activated elements, each element having a first end and a second end, these elements are aligned parallel to each other and disposed radially about the functional tip. These elements are hollow and are made of a material having a high thermal expansion coefficient so that their length changes in proportion to absorbed heat energy to them. A plurality of fiber optic bundles, each bundle having one end attached to the control source and the other end attached to one of the elements, provide light energy to the elements. The end of each bundle which is attached to its respective element may be either inserted within the hollow lumen of that element or connected to that element by a sleeve covering both the element and the end of the bundle. The light energy carried by the optic fiber bundle is converted into heat energy at the elements causing expansion of the elements. If less than all of the elements are heated or the elements are heated differentially, the tip of the catheter will bend away from the element or elements which received the most heat, since those elements ae expanding. By selectively distributing and varying the intensity of light sent to one or more of the elements, the tip of the catheter may be maneuvered.

A feature of the present invention is the compact design, based on optical fibers and direct conversion of light to heat energy for thermal expansion. As a result the catheter can be made very small and, thus, accessible to small diameter pathways. Another advantage of this feature is the additional room provided for optional equipment such as optic fibers for carrying light for observation, tubing, or instrumentation for biopsies and the like, within the lumen of the catheter.

Another feature of the present invention is the ability to selectively apply light of varying intensity to one or more of the elements. This feature permits fine control in the direction and amount of bending resulting in a more maneuverable catheter.

Another feature of the present invention that results in greater maneuverability is the capability of repeated bending and short bending cycles. After the light has been converted into heat to expand the element or elements selected, the heat quickly dissipates and the element or elements return to the original, straight configuration.

Yet another feature of the present invention in a preferred embodiment is a medical instrument located within the lumen of the catheter and deployed and operated by the same light conversion method used for bending the catheter tip, namely thermal expansion. A biopsy instrument, for example, located within the catheter may be advanced to the desired location within the vessel or organ, then light directed to an element associated with the biopsy instrument causes that element to expand forcing the biopsy instrument to close around and snip a portion of the desired tissue. The element associated with the biopsy instrument is similar in its response to light as an element of the catheter tip.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

FIG. 1 is a perspective view of a catheter according to a preferred embodiment of the present invention;

FIG. 2 is a partial cross sectional view of the tip of a catheter according to a preferred embodiment of the present invention;

FIG. 3 is a partial cross sectional view of the tip of the catheter of FIG. 2 when light is supplied to the expandable elements;

FIG. 4 is a cross sectional view of the catheter of FIG. 2;

FIG. 5 is a cross sectional end view of the catheter of FIG. 4 along the line 5—5;

FIG. 6 is a cross sectional end view of the catheter of FIG. 4 along the line 6—6;

FIG. 7 is a cross sectional end view of the catheter of FIG. 4 along the line 7—7;

FIG. 8 is a cross sectional end view of the catheter of FIG. 4 along the line 8—8;

FIG. 9 is a perspective of a catheter according to an alternative embodiment of the present invention with a biopsy instrument within the lumen; and FIG. 10 is a perspective of the alternative catheter of FIG. 9 with the biopsy instrument extended.

DETAILED DESCRIPTION OF A PREFERRED EMBODIMENT

In the following description similar components are referred to by the same reference numeral in order to simplify the understanding of the sequential aspect of the drawings.

Referring now to FIG. 1, shown in perspective is the embodiment of the present invention, a medical catheter 10. Catheter 10 has a first end 12 and a functional tip 14. First end 12 is connected to a control source 16. Control source 16 may be a control system comprising a light supply source in conjunction with a controlling mechanism of known means (e.g., a "joystick", a tactile membrane switch as shown, a ball controller, or other suitable control means). Catheter 10 is covered with a flexible sheath 18 of suitable material which can withstand heat, is flexible, and provides thermal insulation. Plastic, Teflon, and polyethylene are examples of such suitable material. As seen in FIGS. 2 and 3, functional tip 14 contains a plurality of elements 20. Each element 20 is a hollow cylinder and has a first end 22 and a second end 24. Elements 20 are preferably of the same length, arranged parallel to each other and the long axis of catheter 10 and deployed radially about functional tip 14. First ends 22 of elements 20 are supported by a rigid first support means 34, while second ends 24 are supported by a rigid second support means 36. Each fiber optic bundle 26 is attached to, and preferably enters, first end 22 of each element 20. Each bundle 26 is in optical communication with control source 16 to carry light from control source 16 to each element 20. When no light is supplied by control source 16, each element 20 is generally at the same temperature and straight. First support means 34 and second support means 36 are also preferably parallel to each other and more or less perpendicular to elements 20. First and second support means may be made of any material with a low coefficient of thermal conductivity, such as stainless steel. When light is supplied to less than all of elements 20 in functional tip 14, those elements 20 expand as light energy is absorbed as heat energy thereby causing functional tip 14 to bend in a direction away from those elements 20. Each fiber optic bundle 26 communicates between control source 16 and the appropriate element 20. When control source 16 sends light through fiber optic bundles 26, the interior of hollow elements 20 to which the light has been sent absorbs the light thereby converting the light into heat which causes that element 20 to expand. Because that element 20 is anchored within sheath 18 by first support means 34 and second support means 36, the expansion effectively causes support 34 and 36 to bow away from each other, out of a parallel spatial relationship, thus turning the tip of the catheter in the direction opposite the expanding element. By selectively distributing light to one or more fiber optic bundles, the direction of the tip of the catheter may be controlled. By varying the intensity of light distributed to a selected fiber optic bundle. more expansion is possible, causing more bending of the catheter tip.

This bending action is illustrated in FIG. 3. Element 20 is made of a material with a high coefficient of expansion, such as silver, hard drawn copper, aluminum, or an appropriate alloy, and acts as a "black body" to convert incident light into heat. The increase in temperature within element 20 as a result of absorbed heat causes it to expand and lengthen. Because first support means 34 and second support means 36 hold element 20, the heated element 20 must bow or bend upon expanding. The effect of this expansion is to bend the tip 14 away from the expanding element 20.

FIG. 4 depicts catheter 10 in cross section within a branching blood vessel. Elements 20 are shown between first support means 34 and second support means 36 within functional tip 14. First end 22 of each element 20 is located closer to first end 12 of catheter 10 and second end 24 of each element 20 is located closer to functional tip 14 of catheter 10. A fiber optic bundle 26 joins first end 22 of each element 20 with control source 16. The proximal end 28 of a given fiber optic bundle 26 contacts control source 16 and the distal end 30 of that fiber optic bundle 26 contacts a given element 20 to permit the flow of light through fiber optic bundle 26. By selectively passing light through one or more fiber optic bundles 26, one or more elements 20 expand, and functional tip 14 is bent. Elements 20 are supported within functional tip 14 by a first support means 34 located within the periphery of functional tip 14 and a second support means 36 also located within the periphery of functional tip 14 and further from first end 12 of catheter. Support means 34 and 36 are circular and made of a rigid material with a low coefficient of expansion, such as stainless steel. Support means 34 and 36 hold elements 20 in spaced relation when elements regardless of the amount of heat applied; hence when one or more element 20 receives more light than the other, the functional tip bends.

As shown in FIG. 5, this embodiment has four fiber optic bundles 26 within flexible sheath 18, however, any number of fiber optic bundles may be located within the periphery of catheter 10. Preferably the bundles would be located equidistantly about the periphery.

In FIG. 6 first support means 34 is depicted within flexible sheath 18. First support means 34 rigidly contacts each element 20. Each element 20 accepts distal end 30 of its respective fiber optic bundle 26 in a light-tight connection.

In FIG. 7 elements 20 are depicted in the periphery of sheath 18. Each element 20 is hollow, with an interior that absorbs the light energy passed from fiber optic bundle 26. As a given element 20 is provided with light from control source 16 along the corresponding fiber optic bundle 26, the light energy is converted into heat energy and that element 20 expands, causing functionall tip 14 to bend away from that element 20.

FIG. 8 is a cross section through catheter 10 at line 8—8 of FIG. 4. This portion of functional tip 14 is composed only of sheath 18. This portion of functional tip 14 is quite flexible so that it may deform when making first contact with the wall of the vessel or pathway through which catheter 10 is traveling.

As illustrated in FIGS. 9 and 10, several medical instruments may be carried by catheter 10. In FIG. 9, a biopsy instrument 50 is shown within the lumen 52 of catheter 10. Instrument 50 in the closed position rests inside tip 14. When the desired biopsy site is reached with catheter 10, instrument 50 is extended from tip 14 via a slit passage 54 in tip 14. An additional fiber optic bundle 56 connected to an element 58 may transport light for conversion into heat causing expansion of element 58 in contact with instrument 50 thereby extending instrument 50.

FIG. 10 depicts instrument 50 extended and opened. As instrument 50 extends through slit passage 54, movable jaws 60 open allowing selected tissue to be sampled or snipped. When the light source is interrupted, element 58 retracts and instrument 50 returns within catheter 10 with the tissue sample in jaws 60. Other medical instruments may be placed in the lumen 52 of catheter 10 as well. These other instruments may also be remotely operated through fiber optic bundles to elements that convert the light from the fiber optic bundle causing the elements to expand and variously operate the instruments.

While the invention has been described in terms of what is presently regarded as the preferred embodiment, it will be understood by those of ordinary skill in the art that various modifications and changes may be made which will nevertheless remain within the spirit and scope of the invention as defined by the claims which follow.

What is claimed is:

1. A catheter comprising:
   a control source;
   a flexible tube having a first end and an opposing functional tip, said first end connected to said control source;
   a plurality of elements, each element having a first end and a second end, said plurality of elements disposed about said functional tip;
   a plurality of fiber optic bundles for selectively heating each element of said plurality of elements, said optic bundles having a proximal end and a distal end, said proximal end attached to said control source and said distal end attached to one of said elements, said optic bundles directing any light carried by said bundles into said elements, said each element expanding upon being heated; and
   means for bending said functional tip as one or more of said each element expands, said bending means operatively connected to said plurality of elements.

2. The catheter as recited in claim 1, wherein said bending means further comprises at least two rigid support members, a first support member attached to said first ends of said elements and a second support member attached to said second ends of said elements, said first support member holding said first ends in spaced relation and said second support member holding said second ends in spaced relation, whereby said functional tip bends as said heating means heats said elements selectively.

3. The catheter as recited in claim 1, wherein said control source further comprises:
   a light source and
   means for distributing light from said light source selectively to any one or more of said fiber optic bundles.

4. The catheter as recited in claim 3, wherein said distributing means further comprises means for varying the intensity of said light distributed to said optic fibers.

5. A catheter for use with a plurality of light sources, said catheter comprising:
   a flexible tube having a first end and an opposing functional tip;
   a plurality of optical fibers carried by said flexible tube from said first end to said functional tip, each of said optical fibers in optical connection with one of said plurality of light sources;
   a plurality of elements, each element having a first end and a second end, said plurality of elements arranged in parallel and disposed longitudinally about said functional tip, said elements expanding when heated, said first end of each of said plurality of elements connected to one of said plurality of optical fibers so that any light carried by said optic fibers is received by said elements; and
   means for bending said functional tip when said elements are heated, said bending means operatively connected to said plurality of elements.

6. The cathether as recited in claim 5, wherein said bending means further comprises at least two rigid support members, a first support member attached to said first ends of said elements and a second support member attached to said second ends of said elements, said first support member holding said first ends in spaced relation and said second support member holding said second ends in spaced relation, said functional tip bending as light from said light sources, carried by said optic fibers, is received by said elements.

7. The catheter as recited in claim 5, further comprising an instrument carried by said functional tip and means for deploying said instrument, said deploying means carried within said catheter.

8. A maneuverable catheter, comprising:
   a control source;
   a flexible tube having a first end and an opposing functional tip, said first end in operational connection with said control source;
   means carried by said functional tip for expanding said functional tip in response to changes in temperature of said expansion means;
   first means for heating said expanding means, said heating means operatively connected to said control source and adapted to heat different portions of said expanding means at different rates so that said expanding means bends, said heating means comprising a plurality of optical fibers connected to different portions of said expanding means so that any light carried by said fibers is received by said expanding means whereby said expanding means converts said light to heat;
   an instrument carried by said functional tip; and means for deploying said instrument. said deploying means carried within said catheter.

9. The catheter as recited in claim 8. wherein said deploying means further comprises:
    an element that expands when heated. said element carrying said instrument;
    second heating means for heating said element so that said element expands. said second heating means operatively connected to said control source; and
    means formed in said functional tip for allowing said instrument t exit and enter said functional tip.

10. The catheter as recited in claim 8, wherein said control source further comprises means for distributing different amounts of light among said optical fibers so that the light received by said optical fibers heats said different portions of said expanding means to different extents.

11. The catheter as recited in claim 8. wherein said expanding means further comprises:
    elements in communication with said control source. each of said elements having a first end and a second end, said elements expanding when heated; and
    means for connecting said first ends together in spaced relation and said second ends together in spaced relation so that as said elements expand, said first ends and said second ends maintain said spaced relations.

12. The catheter as recited in claim 11, wherein said elements are heated by said control source in different amounts so that said functional tip bends as said elements expand.

* * * * *